(12) United States Patent
Malkowski

(10) Patent No.: US 10,905,854 B2
(45) Date of Patent: *Feb. 2, 2021

(54) SURGICAL ARTICULATION ASSEMBLY

(71) Applicant: Covidien LP, Mansfield, MA (US)

(72) Inventor: Jaroslaw T. Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 88 days.

This patent is subject to a terminal disclaimer.

(21) Appl. No.: 16/161,121

(22) Filed: Oct. 16, 2018

(65) Prior Publication Data

US 2019/0046768 A1 Feb. 14, 2019

Related U.S. Application Data

(63) Continuation of application No. 15/057,758, filed on Mar. 1, 2016, now Pat. No. 10,130,793, which is a continuation of application No. 13/735,063, filed on Jan. 7, 2013, now Pat. No. 9,271,701.

(60) Provisional application No. 61/584,692, filed on Jan. 9, 2012.

(51) Int. Cl.
*A61B 17/00* (2006.01)
*A61M 25/01* (2006.01)
*A61B 17/34* (2006.01)
*A61B 17/068* (2006.01)

(52) U.S. Cl.
CPC ......... *A61M 25/0113* (2013.01); *A61B 17/00* (2013.01); *A61B 17/3421* (2013.01); *A61B 17/068* (2013.01); *A61B 2017/0069* (2013.01); *A61B 2017/00314* (2013.01)

(58) Field of Classification Search
CPC .............. A61B 17/00; A61B 17/00234; A61B 2017/00314; A61B 2017/00318; A61B 2017/00327; A61B 2017/00477; A61B 2017/00681; A61B 2017/0069; A61M 25/01; A61M 25/0105; A61M 25/0113; A61M 25/01133; A61M 25/01138; A61M 25/0141; A61M 25/0147
USPC ..................................................... 606/1, 130
See application file for complete search history.

(56) References Cited

U.S. PATENT DOCUMENTS

| | | |
|---|---|---|
| 4,898,577 A | 2/1990 | Badger et al. |
| 4,998,916 A | 3/1991 | Hammerslag et al. |
| 5,007,434 A | 4/1991 | Doyle et al. |
| 5,030,204 A | 7/1991 | Badger et al. |

(Continued)

*Primary Examiner* — Ahmed M Farah
(74) *Attorney, Agent, or Firm* — Carter DeLuca & Farrell LLP

(57) ABSTRACT

A surgical articulation assembly is disclosed, including a control assembly and an articulable portion. The articulable portion includes at least two segments capable of independent movement. The control assembly defines an axis and three user controls configured to be engaged by an operator. Disposed within the control assembly are three pairs of diametrically opposed driving members that effects translation of a connecting member upon engagement of the user controls. An end of the connecting member is attached to one of the first and second segments of the articulable portion. As the connecting member translates with the driving members, the three user controls allow an operator to exert forces at points along the articulable portion. Also disclosed is a method of effecting articulation of a surgical articulation assembly.

19 Claims, 14 Drawing Sheets

(56) References Cited

U.S. PATENT DOCUMENTS

| | | | |
|---|---|---|---|
| 5,306,245 | A | 4/1994 | Heaven |
| 5,441,483 | A | 8/1995 | Avitall |
| 5,507,725 | A | 4/1996 | Savage et al. |
| 6,068,621 | A | 5/2000 | Balceta et al. |
| 6,923,813 | B2 | 8/2005 | Phillips et al. |
| 7,250,027 | B2 | 7/2007 | Barry |
| 7,608,056 | B2 | 10/2009 | Kennedy, II |
| 7,637,903 | B2 | 12/2009 | Lentz et al. |
| 7,682,319 | B2 | 3/2010 | Martin et al. |
| 7,811,277 | B2 | 10/2010 | Boulais |
| 9,017,314 | B2 | 4/2015 | Malkowski et al. |
| 9,259,240 | B2 | 2/2016 | Malkowski et al. |
| 9,271,701 | B2 * | 3/2016 | Malkowski ............ A61B 17/00 |
| 9,351,751 | B2 | 5/2016 | Malkowski |
| 10,130,793 | B2 * | 11/2018 | Malkowski ............ A61B 17/00 |
| 2002/0045915 | A1 | 4/2002 | Balceta et al. |
| 2003/0149422 | A1 | 8/2003 | Muller |
| 2005/0240193 | A1 | 10/2005 | Layne et al. |
| 2005/0273084 | A1 * | 12/2005 | Hinman ................ A61B 1/008 606/1 |
| 2007/0270679 | A1 | 11/2007 | Nguyen et al. |
| 2008/0064921 | A1 * | 3/2008 | Larkin .................... A61B 1/05 600/104 |
| 2009/0043299 | A1 | 2/2009 | Racz |
| 2010/0004591 | A1 | 1/2010 | Barenboym et al. |
| 2010/0121147 | A1 | 5/2010 | Oskin et al. |
| 2014/0005681 | A1 * | 1/2014 | Gee ................ A61B 17/320092 606/130 |

* cited by examiner

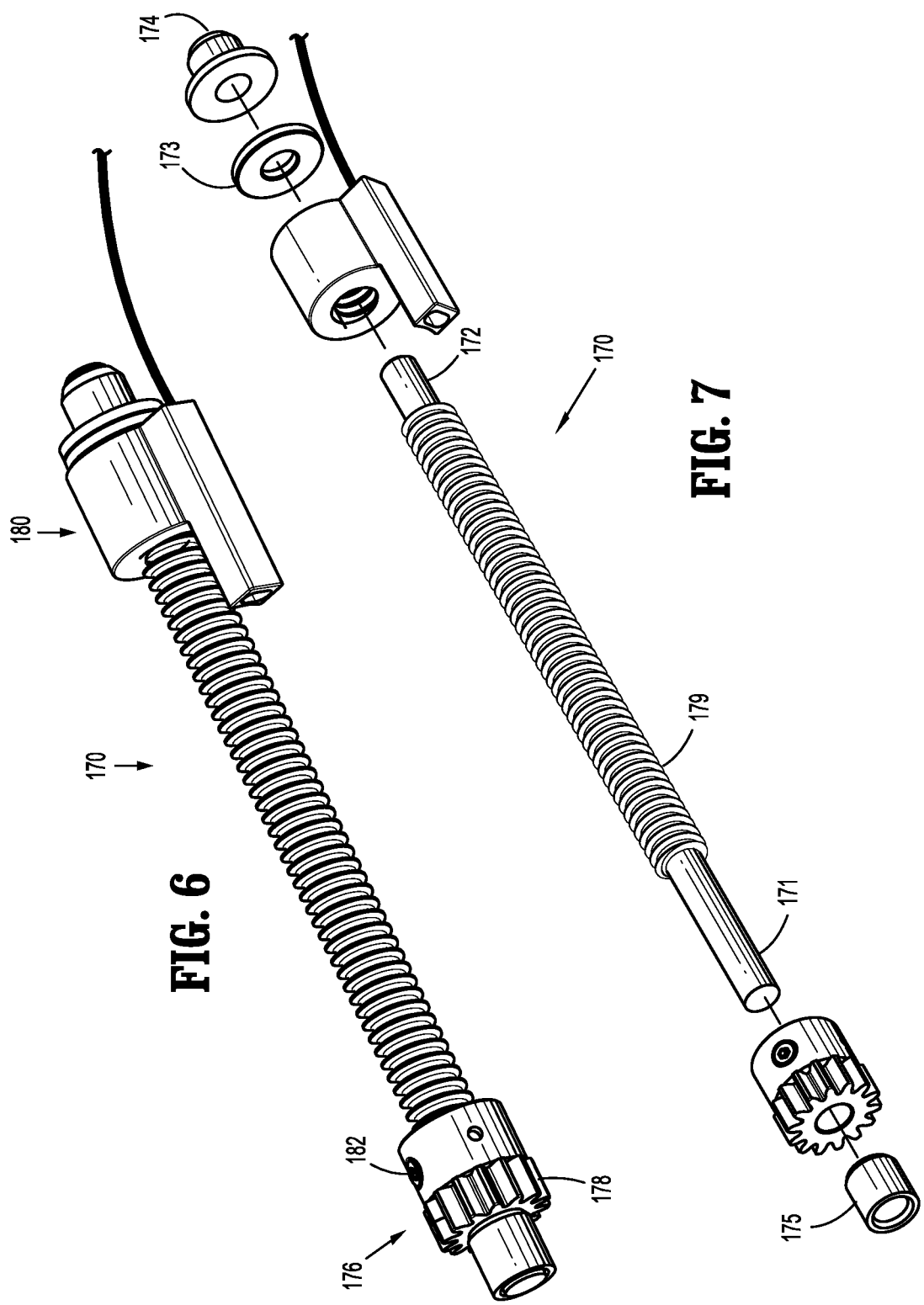

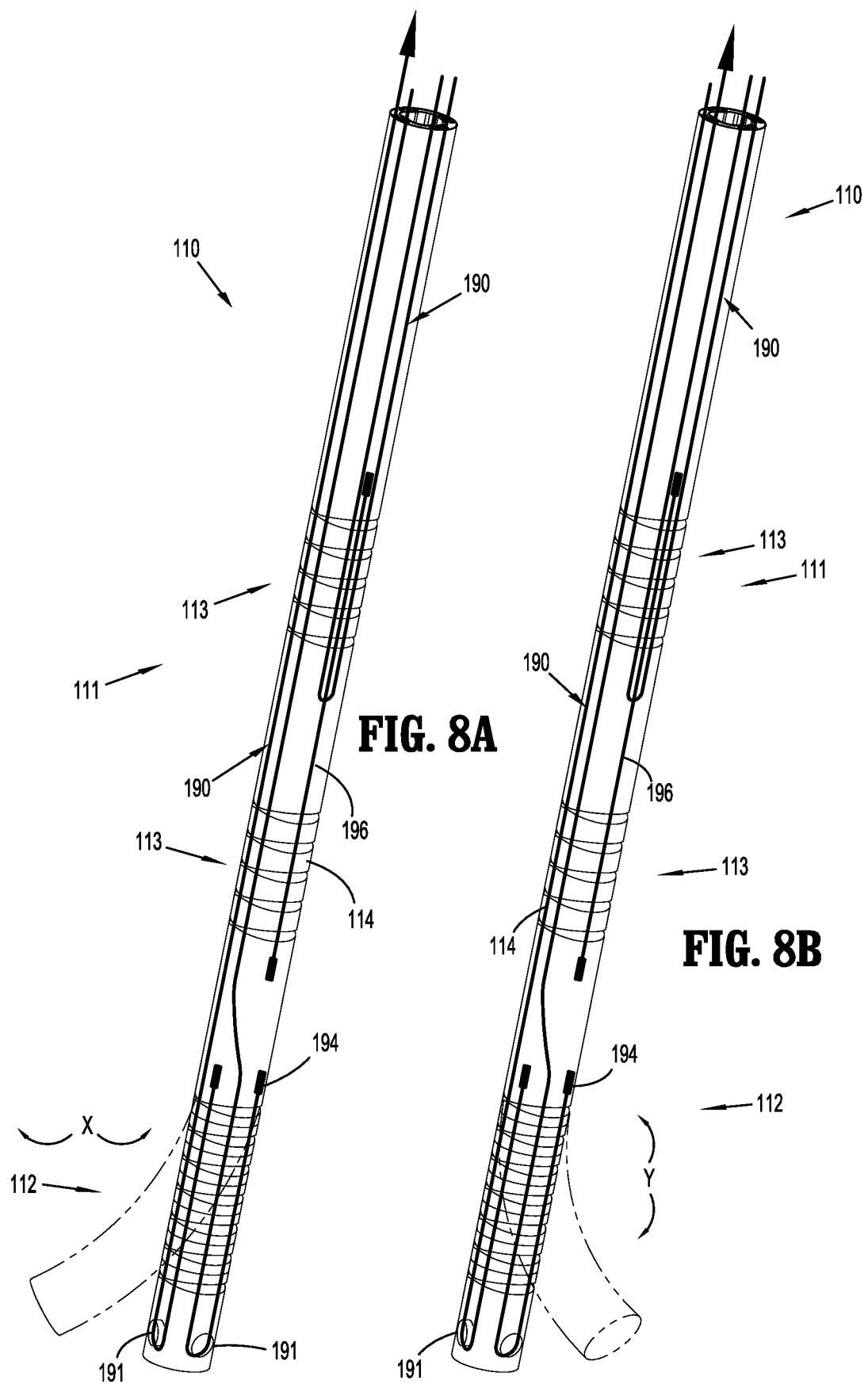

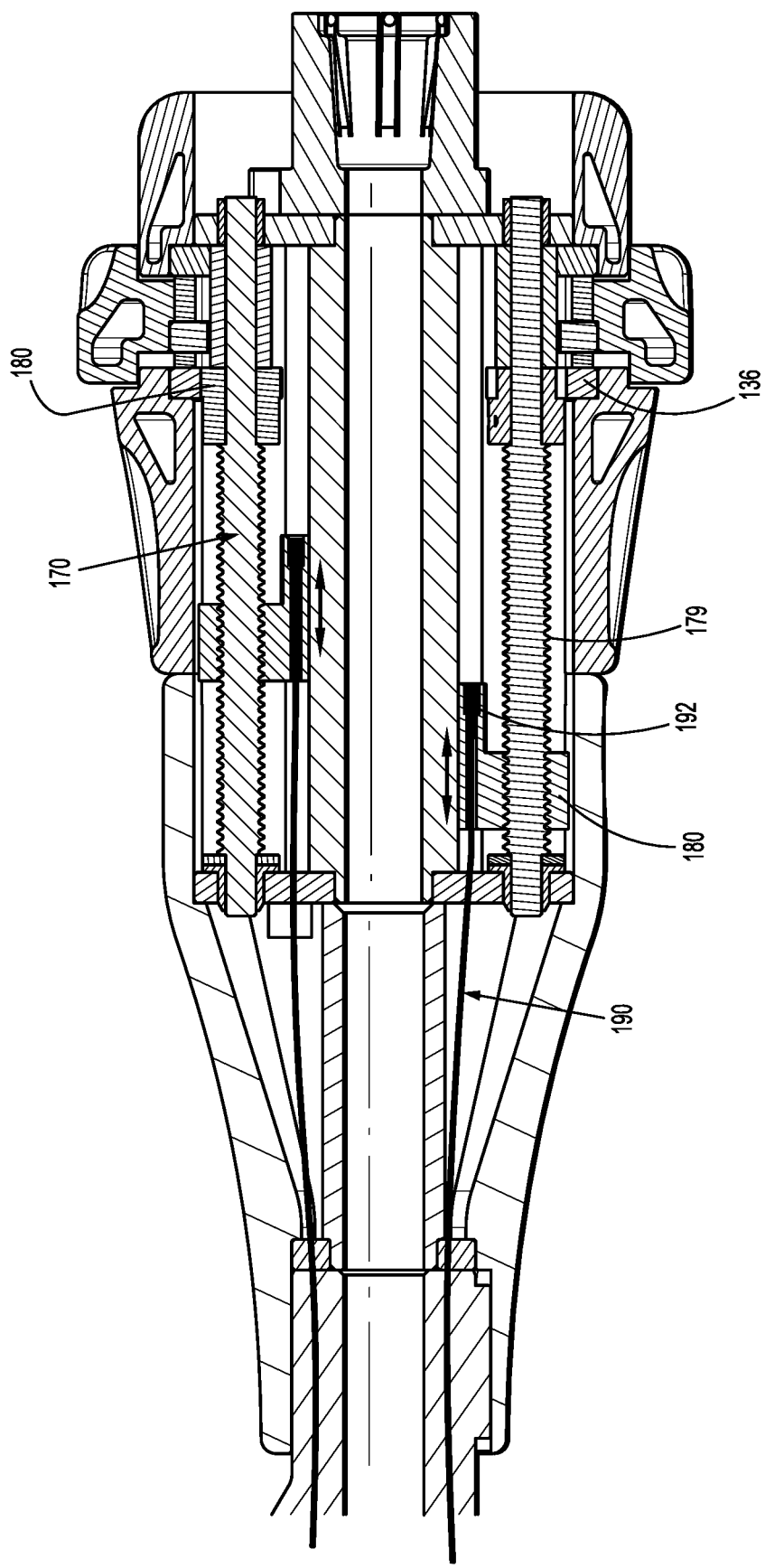

SURGICAL ARTICULATION ASSEMBLY

CROSS-REFERENCE TO RELATED APPLICATIONS

This application is a continuation of U.S. patent application Ser. No. 15/057,758 filed Mar. 1, 2016, which is a continuation of U.S. patent application Ser. No. 13/735,063 filed Jan. 7, 2013, now U.S. Pat. No. 9,271,701, which claims the benefit of and priority to U.S. Provisional Patent Application No. 61/584,692, filed Jan. 9, 2012, the disclosures of each of the above-identified applications are hereby incorporated by reference in their entirety.

BACKGROUND

Technical Field

The present disclosure relates generally to a surgical device for use in a minimally invasive surgical procedure. More particularly, the present disclosure relates to an articulating surgical assembly having at least a first segment and a second segment that are separately movable.

Background of Related Art

A minimally invasive surgical procedure is one in which a surgeon enters a patient's body through one or more small opening in the patient's skin or a naturally occurring opening (e.g., mouth, anus, or vagina). As compared with traditional open surgeries, minimally invasive surgical procedures have several advantages and disadvantages. Minimally invasive surgeries include arthroscopic, endoscopic, laparoscopic, and thoracic surgeries. Advantages of minimally invasive surgical procedures over traditional open surgeries include reduced trauma and recovery time for patients.

However, some disadvantages include a lack of direct visualization of the surgical site and reduced dexterity of instruments, as compared to traditional open surgeries. Maneuvering surgical instruments with the necessary degree of dexterity for surgical procedures is difficult under these conditions, compounded by the fact that a surgeon often needs to reach off-axis points within a body cavity in the course of minimally invasive procedures. Accordingly, a need exists for a system capable of articulating surgical instrumentation through multiple planes in an internal body cavity with accuracy and precision. It is further desirable to provide a surgeon with a control system that is intuitive and easy to operate to compensate for the lack of direct visualization within a body cavity.

Accordingly, a need exists for a surgical device capable of giving a surgeon control of a surgical instrument in multiple planes of movement.

SUMMARY

A surgical articulation assembly is disclosed, including a control assembly and an articulable portion. The surgical articulation assembly has a passage therethrough for receiving a surgical object. The articulable portion includes at least two segments capable of independent movement.

The control assembly defines an axis and includes an inner housing and an outer housing. The control assembly also includes three user controls configured to be engaged by an operator. Each user control contains an engagement member. Disposed within the control assembly are three pairs of diametrically opposed driving members.

The driving members may be threaded, with each diametrically opposed member having an opposing threading pattern. Disposed along a length of each driving member is a rotatable member having surface features for engaging the engagement members of the user controls. Diametrically opposed driving members have a rotatable member disposed along their axial length to interengage the engagement member within one of the three user controls.

Disposed on an outer surface of the driving members is a translating member that engages a recess of the inner housing, and translates proximally or distally with the rotation of the driving members. The translating members may have an internal thread to threadably engage the driving members. Attached to a portion of each translating member is a portion of a connecting member. Another portion of the connecting member is attached one of the first and second segments of the articulable portion. The connecting members may be flexible or rigid. As the connecting member translates with the translating member axially along the driving members, the three user controls allow an operator to exert opposing forces at three positions along the articulable portion.

In one embodiment, the first user control effects bi-directional articulation of the first segment in a plane X. The first segment may additionally contain a series of coupling members that attach proximal and distal portions of the first segment in a manner such that the proximal and distal portions of the first segment articulate through a substantially similar distance in opposing directions in the same plane. The second user control effects articulation of the second segment in plane X, and the third user control effects articulation of the second segment in a plane Y, plane Y being substantially transverse to plane X.

These and other features of the current disclosure will be explained in greater detail in the following detailed description of the various embodiments.

BRIEF DESCRIPTION OF THE DRAWINGS

Various embodiments of the present disclosure are described hereinbelow with reference to the drawings, wherein:

FIG. 6 is an enlarged detail view of a portion of the actuation assembly as shown in FIG. 4;

FIG. 7 is a parts separated view of the portion of the actuation assembly as shown in FIG. 6;

FIG. 8A is a perspective view of the articulable portion of the surgical articulation assembly of FIG. 1, having a first segment disposed proximally of a second segment, the second segment articulating in a plane X;

FIG. 8B is a perspective view of the articulable portion of the surgical articulation assembly of FIG. 8A, with the second segment articulating in an opposing direction in plane X;

FIG. 12 is an enlarged area of detail view of the control assembly as shown in FIG. 8.

Figure 1:
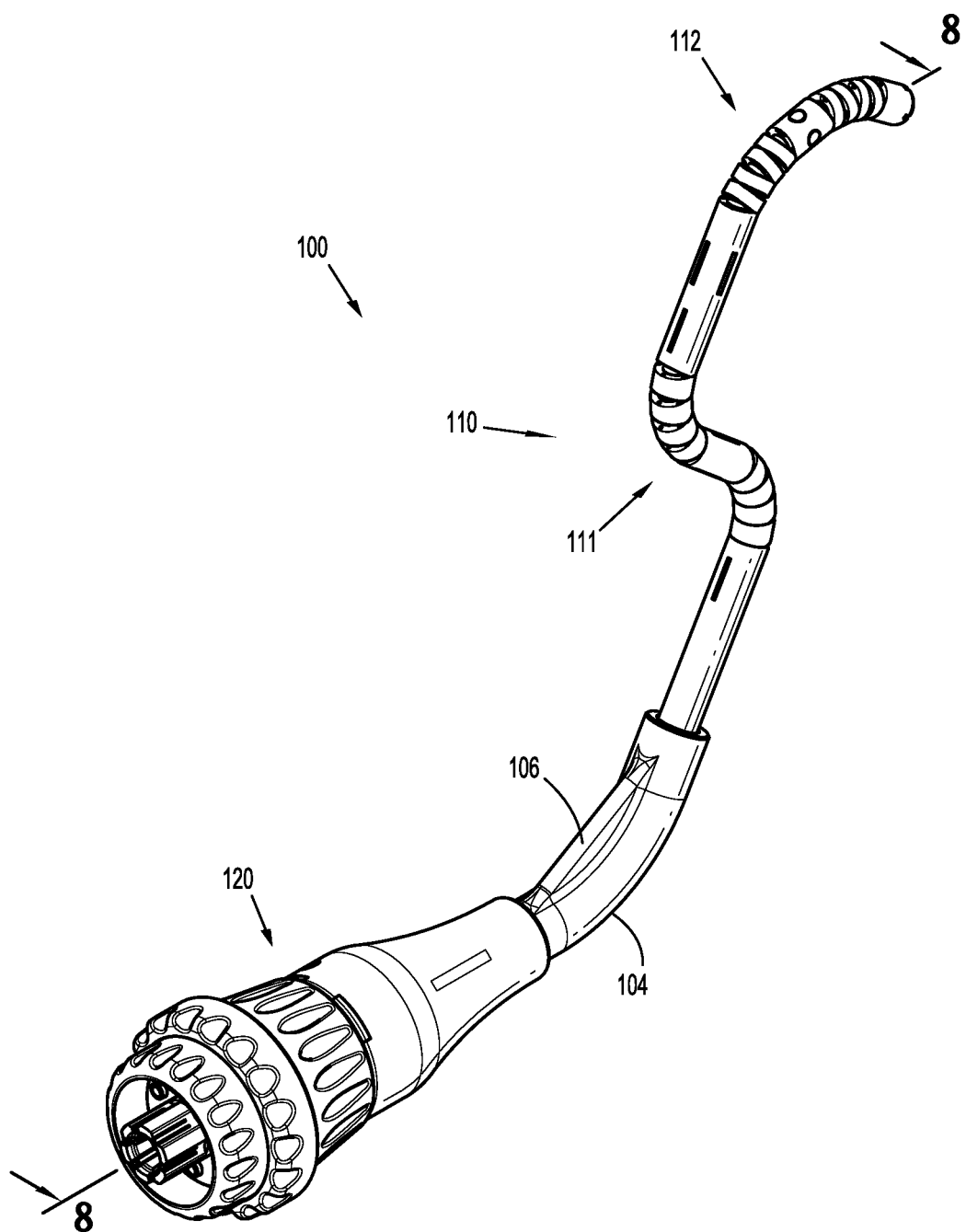
FIG. 1 is a perspective view of a surgical articulation assembly in accordance with the present disclosure.

Other features of the present disclosure will become apparent from the following detailed description taken in conjunction with the accompanying drawings, which illustrate, by way of example, the principles of the present disclosure.

DETAILED DESCRIPTION OF THE EMBODIMENTS

Embodiments of the presently disclosed surgical access assemblies for use in minimally invasive surgery are described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user. The presently disclosed surgical access assemblies are usable in an incision through a patient's tissue, in a naturally occurring orifice (e.g. mouth, anus or vagina), or through an access member.

Figure 8:
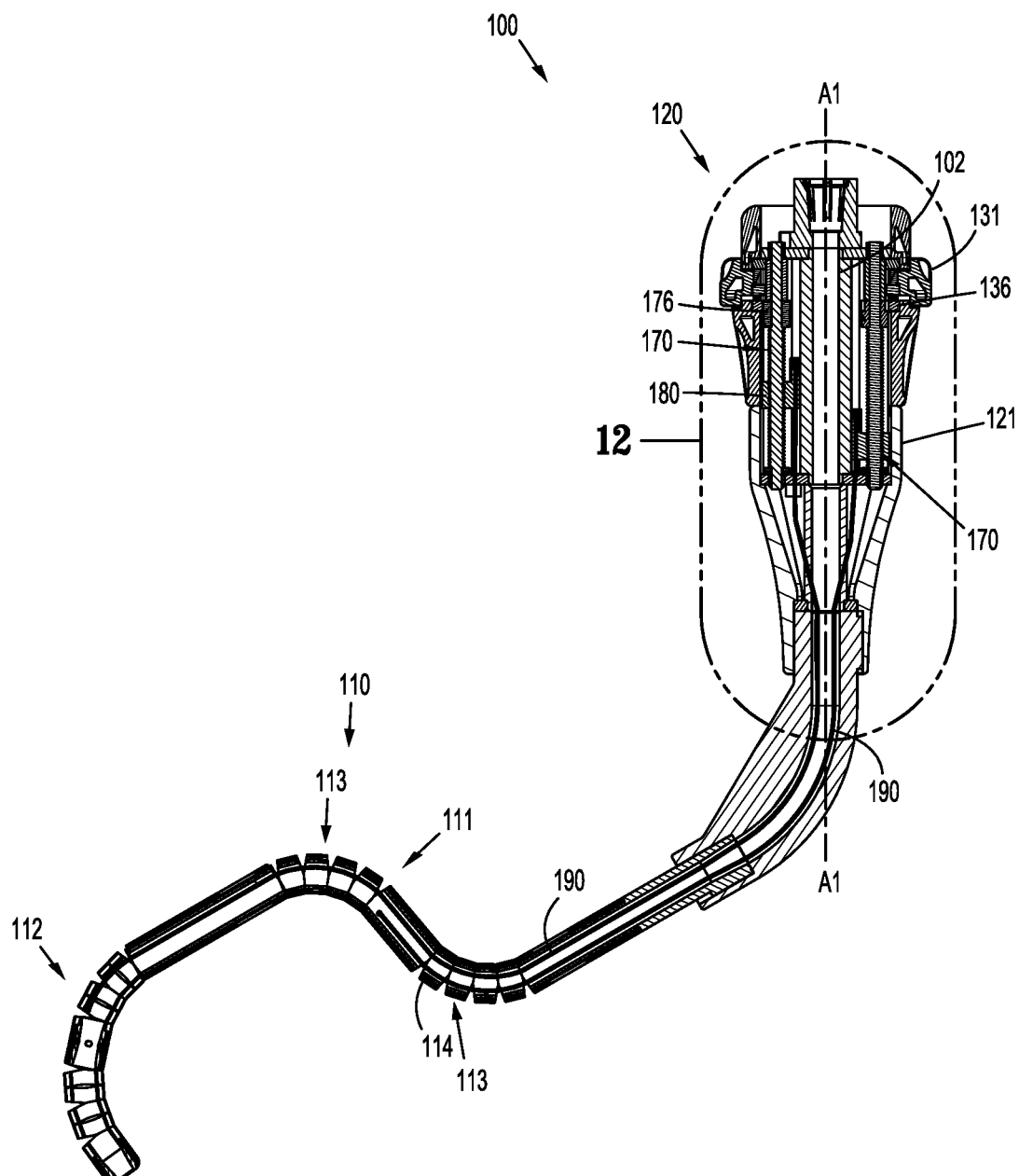
FIG. 8 is a cross-sectional view taken along the line 8-8 of the surgical articulation assembly of FIG. 1.

Referring initially to FIG. 1, a surgical articulation assembly 100 is shown. Surgical articulation assembly 100 includes an articulable portion 110 extending distally from a control assembly 120. Control assembly 120 and articulable portion 110 may be press fit, threaded, adhered, secured with a bayonet-type coupling, or utilize a securing member such as a clamping collar. Control assembly 120 defines a longitudinal axis A1 (FIG. 8). Articulable portion 110 includes at least a first segment 111 and a second segment 112. Second segment 112 is disposed distally of the first segment 111. The first segment 111 and second segment 112 are capable of independent movement relative to the longitudinal axis A1 and to each other, as will be discussed further below.

Figure 2:
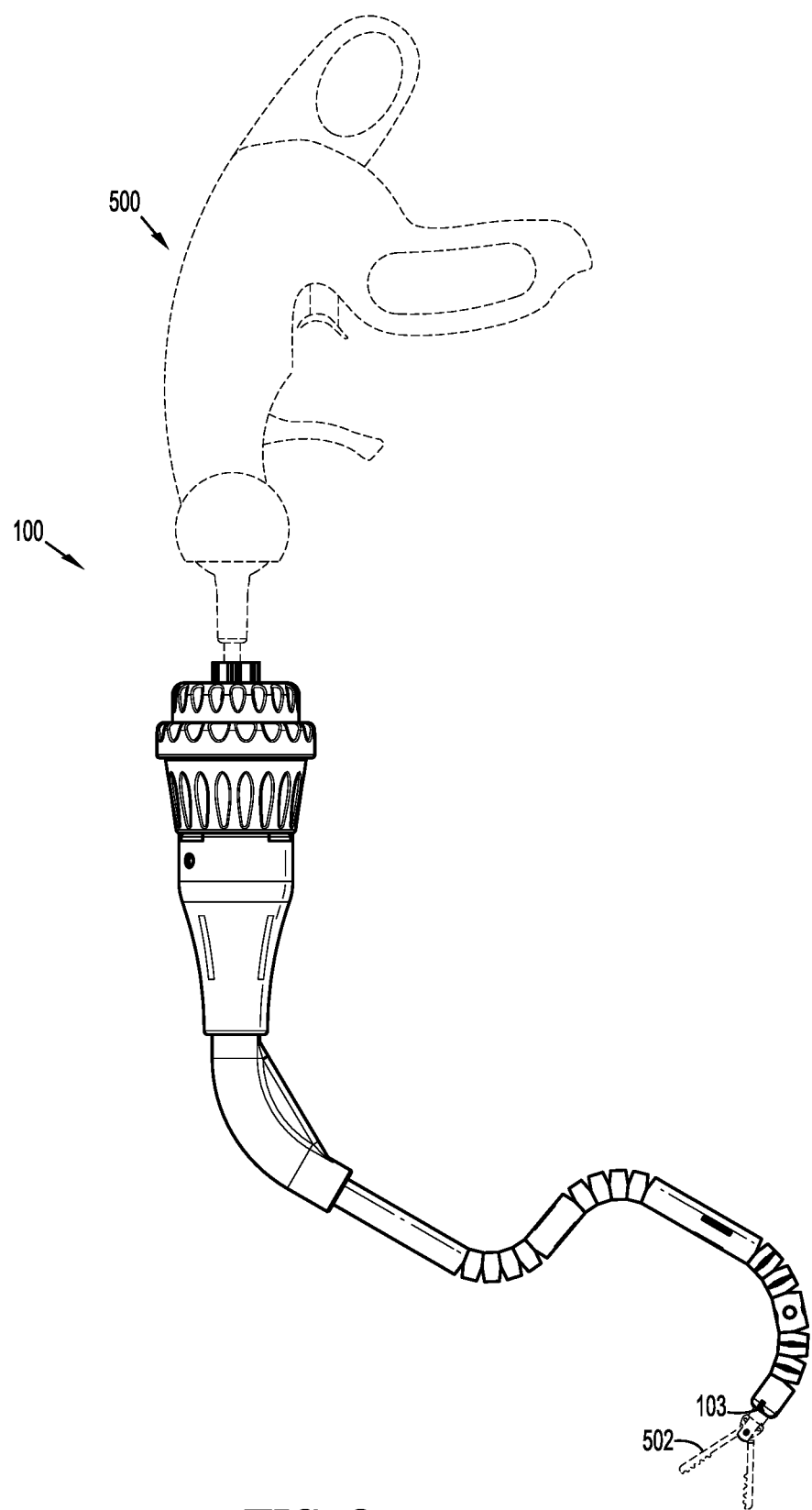
FIG. 2 is a side profile view of the surgical articulation assembly as shown in FIG. 1, with a surgical object having an end effector inserted therethrough.

Turning to FIG. 2, the surgical access assembly 100 is shown in side profile view. Surgical articulation assembly has a passage 102 (FIG. 8) therethrough to receiving a surgical object 500 (shown in phantom view). Surgical object 500 may be an instrument capable of flexion within an articulating member, such as graspers, forceps, probes, scalpels, or staplers. Accordingly, surgical object 500 includes an end effector 502, shown extending through a distal end 103 of the passage 102.

Figure 3:
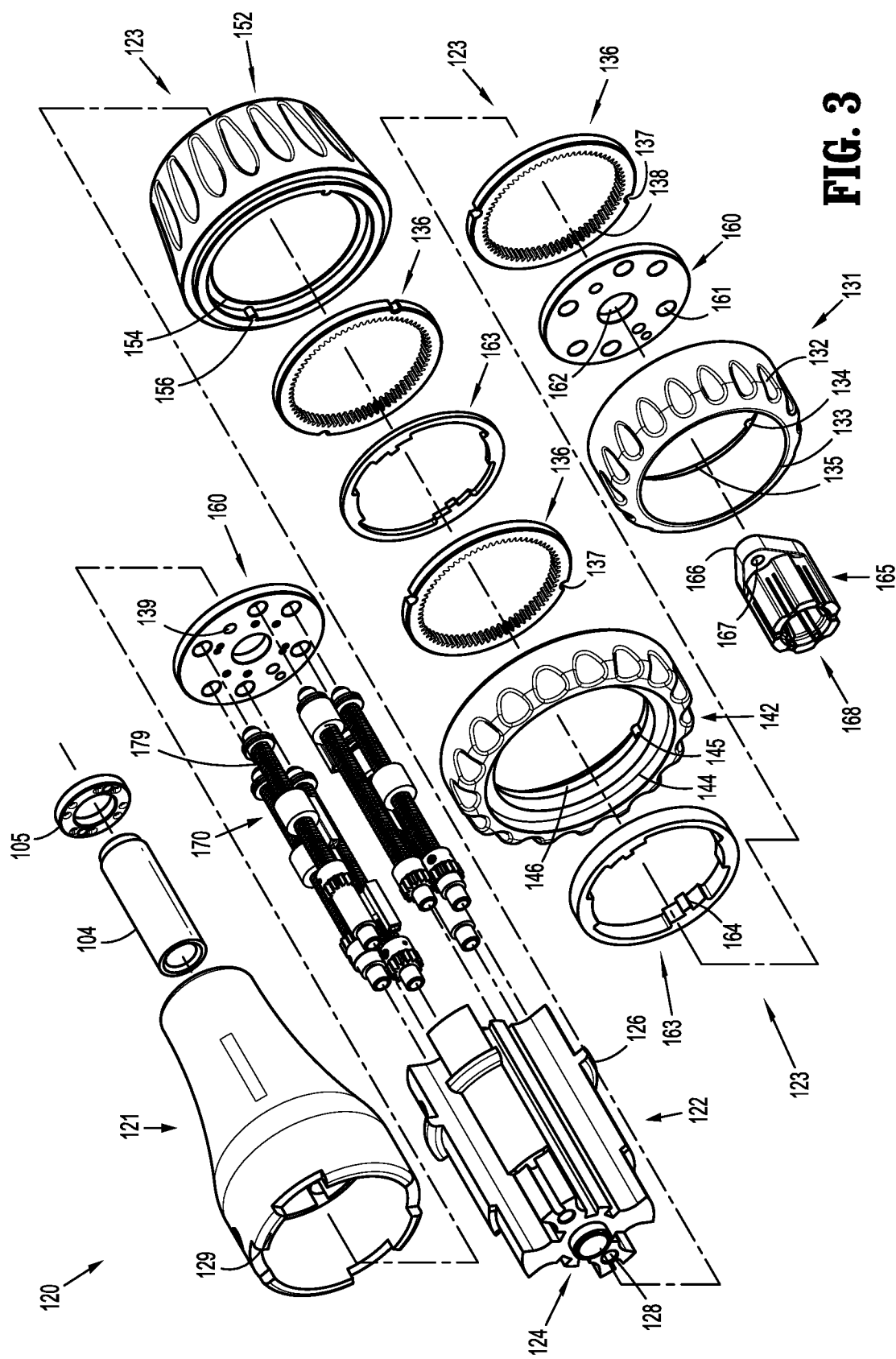
FIG. 3 is a parts-separated view of the control assembly of the surgical articulation assembly as shown in FIG. 1.
Figure 4:
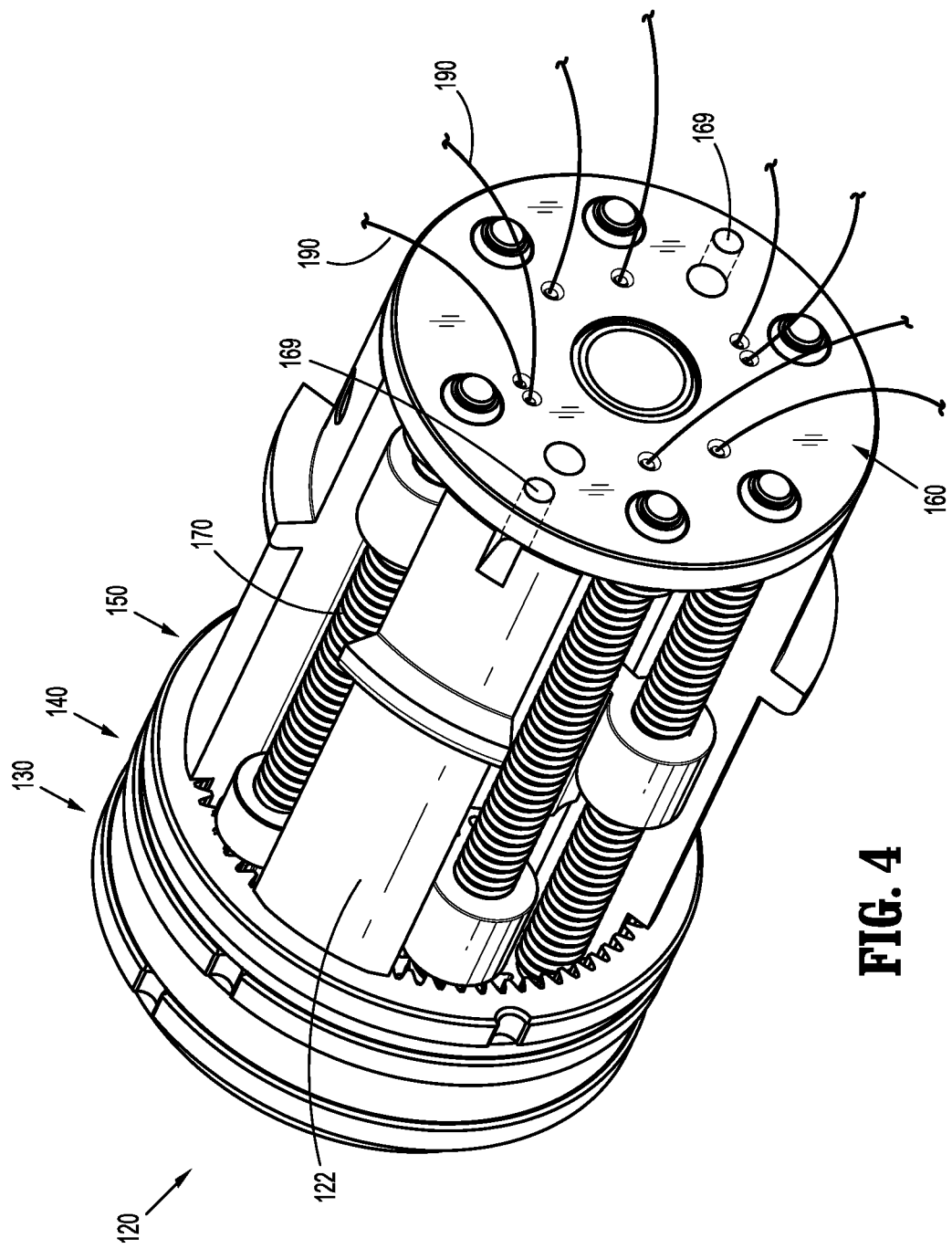
FIG. 4 is an assembled view of a portion of the control assembly as shown in FIG. 3.

Referring to FIG. 3, the control assembly 120 is shown in a parts separated view. Control assembly includes an outer housing 121, an inner housing 122, and three articulation assemblies 130, 140, 150 (FIG. 4). Articulation assembly 130 is disposed proximally of articulation assembly 140, which is disposed proximally of articulation assembly 150. Articulation assemblies 130, 140, 150 include components of control assembly 120 working in cooperation to effect articulation of the first and second segments 111, 112 of articulable portion 110 (FIG. 1), as will be discussed further below. While first, second, and third user articulation assemblies 130, 140, 150 are discussed below having generally circular components, any suitably shaped or profiled components may be used. Further, the components described below may be interengaged and connected by a number of means not limited to the specific structures described below.

Articulation assembly 130 includes a first user control 131, shown here as a knob, but contemplated be any other suitable structure such as a rotary dial or wheel. First user control 131 may have a textured surface 132 to aid an operator in grasping the surface of user control 131. First user control 131 is configured to rotate about longitudinal axis A1 (FIG. 8). Circumferentially disposed within an inner diameter of user control 131 is an anchor plate 160, which engages a proximal rim 133 of the user control 131. Anchor plate 160 includes apertures 161 for receiving other components of the control assembly 120, as will be discussed further below. Anchor plate 160 also contains a central aperture 162 that bounds a portion of passage 102 for receiving a portion of surgical object 500 (FIG. 2). A pair of surface protrusions 134 protrudes from a surface of a distal recess 135 of the first user control 131. Surface protrusions 134 may be tabs as shown, or may be ridges, ledges, or an otherwise textured surface.

An engagement member 136 is circumferentially disposed in the distal recess 135 of user control 131. Engagement member 136 has a pair of recesses 137 that receive surface protrusions 134 such that when user control 131 is rotated about longitudinal axis A1, force is transmitted to engagement member 136, which will also rotate about longitudinal axis A1. Engagement member 136 has a surface geometry 138 that will engage other components of the control assembly 120, as will be discussed further below. Although engagement member 136 is shown here as a planetary gear having teeth disposed on its inner circumference, other configurations are contemplated, such as a frictional wheel or lever arm.

Located distally of user control 131 is a separator plate 163. Separator plate 163 contacts a distal surface of engagement member 136. The interior surface of separator plate 163 includes a series of recesses 164 that contact a portion of inner housing 122, as will be discussed below, to inhibit separator plate 163 from rotating about the longitudinal axis A1. Separator plate 163 and engagement member 136 are formed of materials that minimize frictional forces generated during contact, such as plastics, polished metals, or polymers. A lubricous treatment may additionally be applied between separator plate 163 and engagement member 136 to minimize frictional engagement. Thus, when user control 131 and engagement member 136 are rotated about longitudinal axis A1, they encounter minimal frictional resistance from separator plate 163.

A distal surface of separator plate 163 contacts a user control 142. User control 142 is substantially similar to user control 131, but has a proximal recess 144 in which separator plate 163 is circumferentially disposed. Thus, user controls 131, 142 may independently rotate about the longitudinal axis A1 by virtue of the substantially stationary nature of separator plate 163 with respect to longitudinal axis A1. A second engagement member 136 is disposed in a distal recess 146 of user control 142. A pair of tabs 145 engage recesses 137 of engagement member 136 and transmit forces to the engagement member 136, causing engagement member 136 to rotate about the longitudinal axis A1. Disposed distally of the second engagement member 136 is a second separator plate 163.

Separator plate 163 acts to separate a third engagement member 136, which is circumferentially disposed in a proximal recess 154 of a third user control 152, from the second engagement member 136. Third user control 152 is substantially similar to first and second user controls 131, 142, and the proximal recess 154 includes tabs 156 for receiving the third engaging member 136. The separator plates 163 maintain the independent rotation of first, second, and third user controls 131, 142, 152, and first, second, and third engagement members 136, while minimizing the frictional forces encountered by each during rotation about the longitudinal axis A1.

Figure 7A:
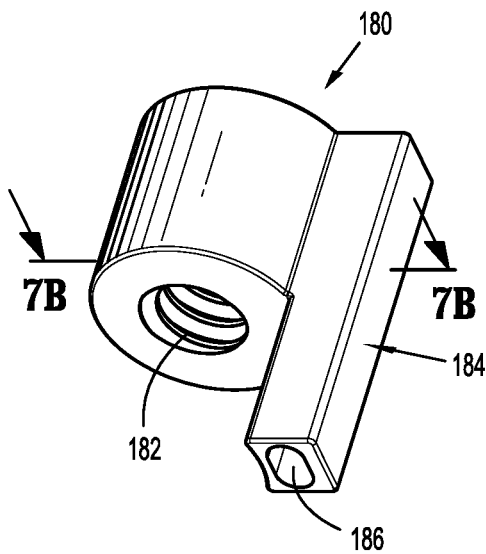
FIG. 7A is an enlarged detail view of the translating member shown in FIG. 7.

First, second, and third user controls 131, 142, 152, and associated components define a channel 123 through which inner housing 122 is disposed. Referring for the moment to FIG. 7C, inner housing 122 is an axial member having a plurality of recesses 124 in its outer circumference. The plurality of recesses 124 are generally in diametrically opposed pairs on inner housing 122, though other shapes and configurations are contemplated for inner housing 122. An outer surface of inner housing 122, between recesses 124, is defined by a ridge 126 to engage a proximal end 129 of outer housing 121 (FIG. 3). Thus, housing 122 ensures that articulation assemblies 130, 140, 150 (FIG. 4) rest proximally above outer housing 121 in a manner such that outer housing 121 does not inhibit the rotation of the components of articulation assemblies 130, 140, 150 about longitudinal axis A1 (FIG. 8). Inner housing 122 also includes a central aperture 127 that bounds a portion of passage 102 (FIG. 8) for receiving a surgical object 500.

Referring back to FIG. 3, the inner housing 122 is shown in relation to the rest of the control assembly 120. Disposed within the recesses 124 of the inner housing 122 are driving members 170. Driving members 170 are axial members that may have surface features 179 to engage additional components, as will be discussed below. Driving members 170 are free to rotate about an axis laterally spaced from the longitudinal axis A1. While driving members 170 are shown here having a threaded surface, other surface configurations such as knurls, teeth, grooves, or spokes are contemplated.

Figure 5:
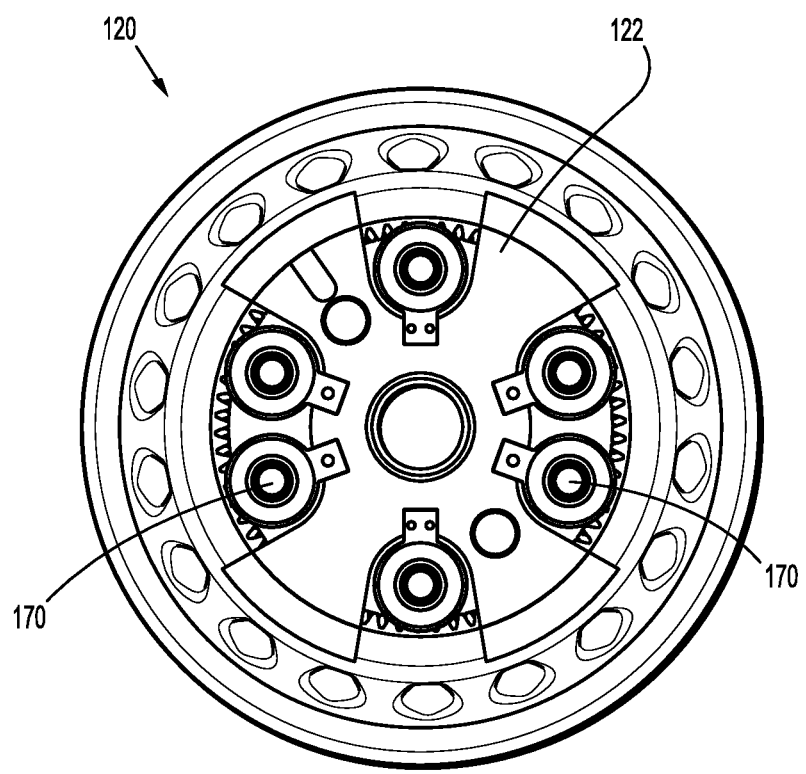
FIG. 5 is a bottom plan view of the control assembly of FIG. 4, with the parts removed.

Turning for the moment to the bottom plan assembly view of FIG. 5, driving members 170 and associated components are disposed in diametrically opposed pairs around inner housing 122. Diametrically opposed pairs of driving members 170 have opposing threading patterns that effect opposing axial forces upon rotation. Therefore, a right-handed threaded driving member 170 is diametrically opposed to a left-handed threaded driving member 170. As will be described further below, the diametrically opposed pairs of driving members 170 cooperate to effect articulation forces on opposing surfaces of the articulable portion 110 (FIG. 1).

Referring for the moment to FIG. 7, driving members 170 may include a separator member 173, such as a washer or spacer, disposed on a distal portion 172, proximally of a distal anchor plate 160 (FIG. 3). Separator member 173 spaces driving members 170 from distal anchor plate 160 and has a surface that inhibits engagement with the outer surface 179 of driving members 170. Thus, the separator member 173 inhibits the axial translation of driving members 170 through the distal anchor plate 160 and maintains the driving members 170 in a substantially stationary axial position. A mounting cap 174 is circumferentially disposed on a distal portion 172 of driving member 170. Mounting cap 174 engages apertures 161 (FIG. 3) of distal anchor plate 160, and has a surface formed of a minimally frictional material such as smooth metal, plastic, or polymer, to minimize frictional engagement with apertures 161. A mounting barrel 175 functions in a similar manner to mounting cap 174 and is circumferentially disposed on a proximal portion 171 of driving member 170. Mounting barrel 175 engages apertures 161 of proximal anchor plate 160 and has a minimal frictional engagement with apertures 161. Thus, driving members 170 are free to rotate within control assembly 120 (FIG. 3) without encountering substantial frictional forces from anchor plates 160. Alternatively, proximal and distal portions 171, 172 of driving members 170 may rotate within mounting barrels 175 and mounting caps 174, respectively, with mounting barrels 175 and mounting caps 174 disposed in apertures 161 by press fit, interference fit, or other secure engagement and inhibited from rotation.

Referring to the detail view of FIG. 6, rotating members 176 are circumferentially disposed around driving members 170, and may be fixed at a position along a length of driving members 170 with a securing member 182, which may be a set screw as shown here, or a pin or clamping collar. Rotating members 176 are additionally secured to driving members 170 such that they do not rotate independently of driving members 170. Alternatively, rotating members 176 may be press fit or interference fit to driving members 170 to prevent the axial translation of and independent rotation of rotating members 176 with respect to driving members 170. Rotating members 176 are fixed at positions along the axial length to align with engagement members 136 (FIG. 3). Rotating members 176 have a textured outer surface 178, shown here as gear teeth, but are also contemplated to include knurls, grooves, or ridges to interengage surface protrusions 138 of engagement members 136 (FIG. 3). Thus, a pair of diametrically opposed driving members 170 align with first, second, or third user controls 131, 142, 152 (FIG. 3).

Circumferentially disposed around the driving members 170 are translating members 180. As shown here, translating members 180 may be cylindrical members configured to be circumferentially disposed on driving members 170. Other shapes and profiles are contemplated for translating members 180. Referring for the moment to FIG. 7A, translating members 180 each contain textured interior surfaces 182, shown here as threads, that engage surfaces 179 of driving members 170 (FIG. 7). Textured surface 182 may have other configurations suitable to engage the outer surfaces of driving members 170. Protruding from a side surface of translating members 180 is a housing 184. Housing 184 is configured to engage a portion of recesses 124 of inner housing 120 (FIG. 3), and translate axially with the rotation of driving members 170. Housing 184 includes an aperture 186 for receiving other components of surgical access assembly 100 (FIG. 1), as will be discussed further below.

Figure 7B:
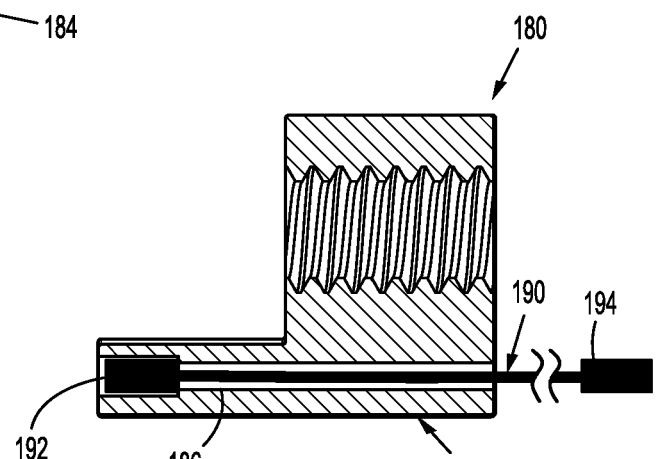
FIG. 7B is a cross-sectional view taken along the line 7B-7B of the translating member shown in FIG. 7A.
Figure 7C:
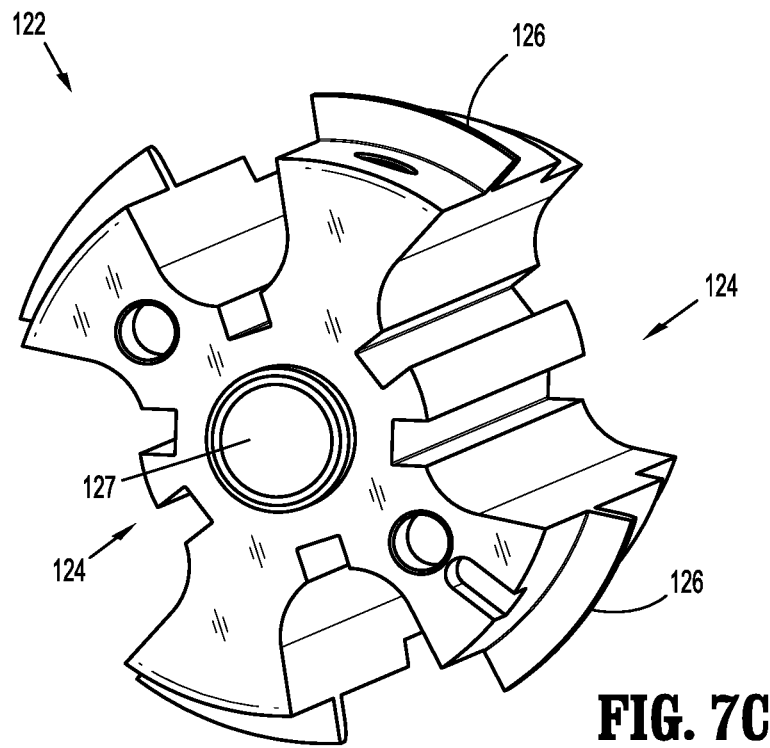
FIG. 7C is an enlarged detail view of the internal housing of the control assembly as shown in FIG. 4.

Turning now to the cross-sectional view of FIG. 7B, a connecting member 190 is shown disposed in the housing 184 of translating member 180. Connecting member 190 may a flexible member such as a cable, as shown here, a wire or string, or may be a rigid member such as a bar. Connecting member 190 has a tensile and/or compressive strength suitable for articulable portion 110 (FIG. 1), as will be discussed further below. Connecting member 190 may have a proximal end 192 for engaging a portion of aperture 186 in housing 184 of translating member 180, and a distal end 194 attached to a portion of articulable portion 110. Proximal end 192 is securely fixed in housing 184 such that connecting member 190 translates axially with translating member 180 along a length of driving member 170 (FIG. 7). Proximal end 192 may be compressively trapped by the geometry of housing 184, and may be defined by a ferrule, as shown here, may be knotted, or may be adhered to or embedded within an interior surface of housing 184.

Referring momentarily to FIG. 4, more than one connecting member 190 may be disposed in housing 184 (FIG. 7A). As seen in a pair of diametrically opposed driving members 170, the presence of two or more connecting members 190 in a housing 184 may offer additional strength for articulation. Alternatively, a connecting member 190 may be looped within aperture 186. Also shown in FIG. 4 is the control assembly 120, fully assembled, without the outer housing 121 and user controls 131, 142, 152 (FIG. 3). To aid in retaining the components of the control assembly 120 in their relative positions, one or more securing members 169 may disposed through anchor plates 160. Securing members 169 may be screws, bolts, pins, or other suitable members, and may connect the anchor plates 160 to the inner housing 122 or extend through a lumen in inner housing 122 and connect the proximal and distal anchor plates 160. When articulation assemblies 130, 140, 150 are assembled, the securing members 169 will hold the respective components in compressed relation within the control assembly 120. Thus, the control assembly 120 may be engaged by an operator without components being forced out of alignment during use in a minimally invasive procedure.

The connecting members 190 extend distally through the distal anchor plate 160 (FIG. 3), and are attached to portions of the articulable portion 110 (FIG. 1), as will be discussed further below. Turning back to FIG. 3, these components are configured to be disposed above outer housing 121, and are prevented from translating below the proximal end of outer housing 121 by the ridge 126 on the inner housing 122. While shown as a tapered cylindrical member, outer housing 121 is contemplated to have a variety of shapes and profiles to accommodate components as needed.

Disposed proximally of the proximal anchor plate 160 is a securing collar 165. Securing collar 165 defines a channel 168 through which a surgical object 500 (FIG. 2) may be inserted. Securing collar 165 includes a pair of flanges 166 that may have apertures 167 for receiving a securing member 169 (FIG. 4).

An extension tube 104 is shown extending from a distal end of housing 121. Extension tube 104 bounds the passage 102 and receives a portion of surgical object 500 (FIG. 2). Extension tube 104 connects control assembly 120 to the articulable portion 110 (FIG. 1). A sealing member 105 may couple control assembly 120 and articulable portion 110, and minimizes the loss of fluids such as insufflation fluids through the connection of extension tube 104 and control assembly 120. Accordingly, sealing member 105 may be a suitable material such as rubber or polymer, and may be configured as an o-ring. Extension tube 104 may be flexible. Referring momentarily back to FIG. 1, a reinforcing member 106 may brace extension tube 104 such that bending forces caused by the articulation of articulable portion 110 do not overstress extension tube 104 causing tearing or breaking. Reinforcing member 106, as shown here, may be a gusset attached to extension tube 104.

Figure 9:
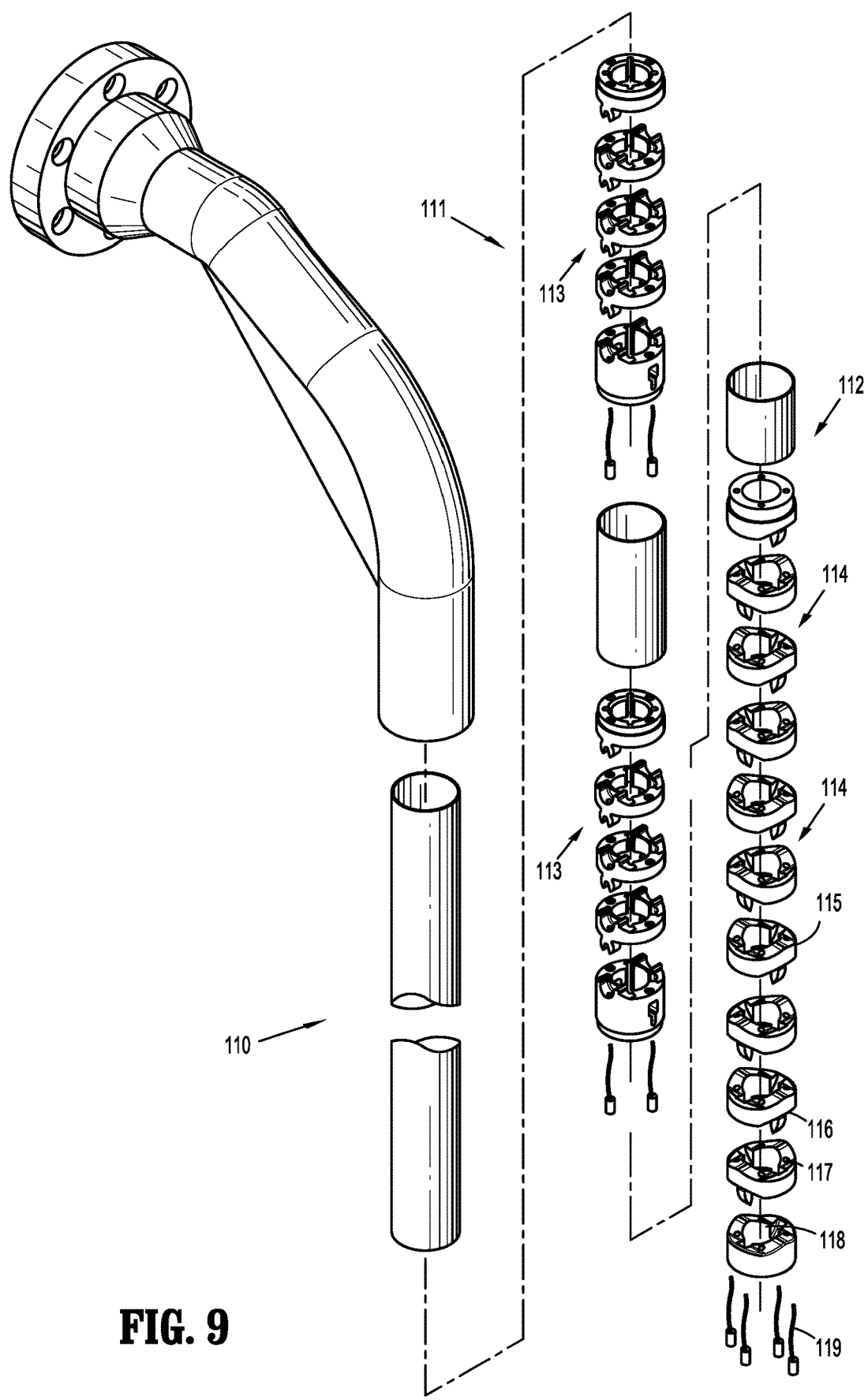
FIG. 9 is a parts separated view of the portion of the articulable portion of the surgical articulation assembly of FIG. 1.

Referring to FIG. 9, a portion of the articulable portion 110 is shown in parts separated view. The first and second segments 111, 112 (FIG. 1) of the articulable portion 110 may be continuous flexible members, or may include independently movable members 114 that, when assembled, engage in a manner such that each movable member 114 is free to pivot relative to an adjacent movable member 114. The first segment 111 includes at least two sets 113 of movable members 114. A first set 113 is located proximally of a second set 113, and the sets 113 are separated by a continuous segment of articulable portion 110. The sets 113 contain the same number of movable members 114 and are configured in the substantially same manner.

Movable members 114 contain surface protrusions 115 and surface recesses 116 to engage adjacent movable members 114. Movable members 114 may be connected with connecting elements 119, which may be disposed through an aperture 117 through movable members 114. Connecting elements 119 may be flexible members such as cables or wires, or may be rigid members such as links. As shown, sections of adjacent movable members 114 may have varying surface protrusions 115 and surface recesses 116 such that a series of adjacent movable members 114 is configured for articulation in one direction, and another series of adjacent movable members 114 is configured for articulation in a different direction. Any number and variable configuration of alternating surface protrusions 115 in a series of movable members 114 is contemplated to optimize articulation in multiple planes. Movable members 114 also contain a central aperture 118 bounding a portion of the passage 102 and receiving a portion of surgical object 500 (FIG. 2).

Figure 10:
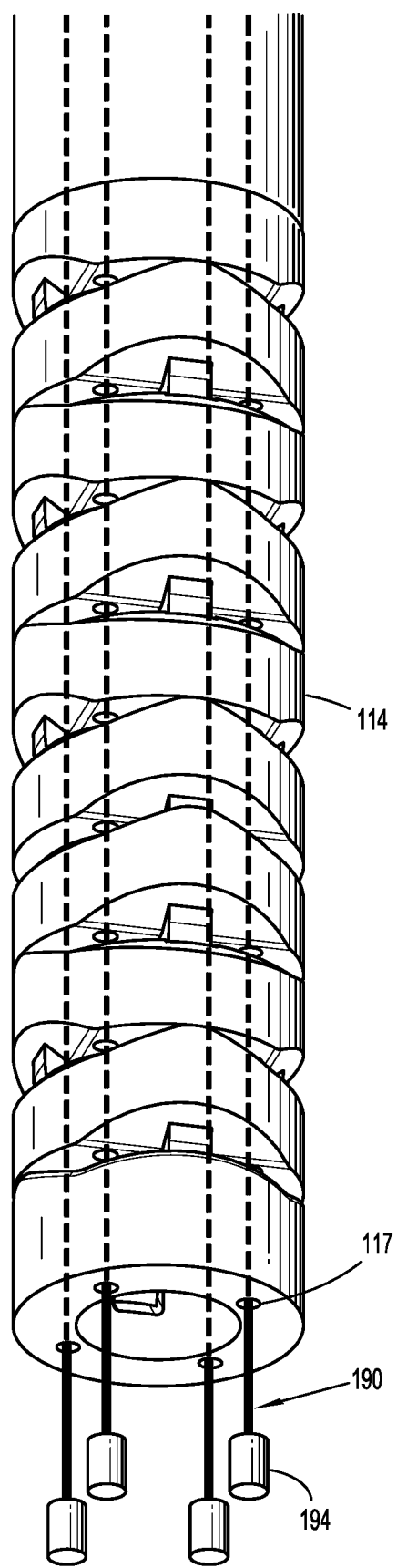
FIG. 10 is an enlarged area of detail view of a series of movable members in section of the articulable portion as shown in FIG. 9.

Referring now to FIG. 10, distal ends 194 of connecting members 190 may be disposed through apertures 117 of the distal movable member 114 of a segment 111, 112 (FIG. 1) in addition to or in place of the connecting elements 119 described above (FIG. 9). A distal end 194 of a connecting member 190 may include a knot or ferrule, as described above with respect to proximal end 192. Alternatively, a distal end 194 may be attached to an internal wall of a segment 111, 112 by adhesion, welding, or looping around an internal structure (not shown). Further, connecting members 190 may be embedded within a surface of articulable portion 110 (not shown).

Figure 8C:
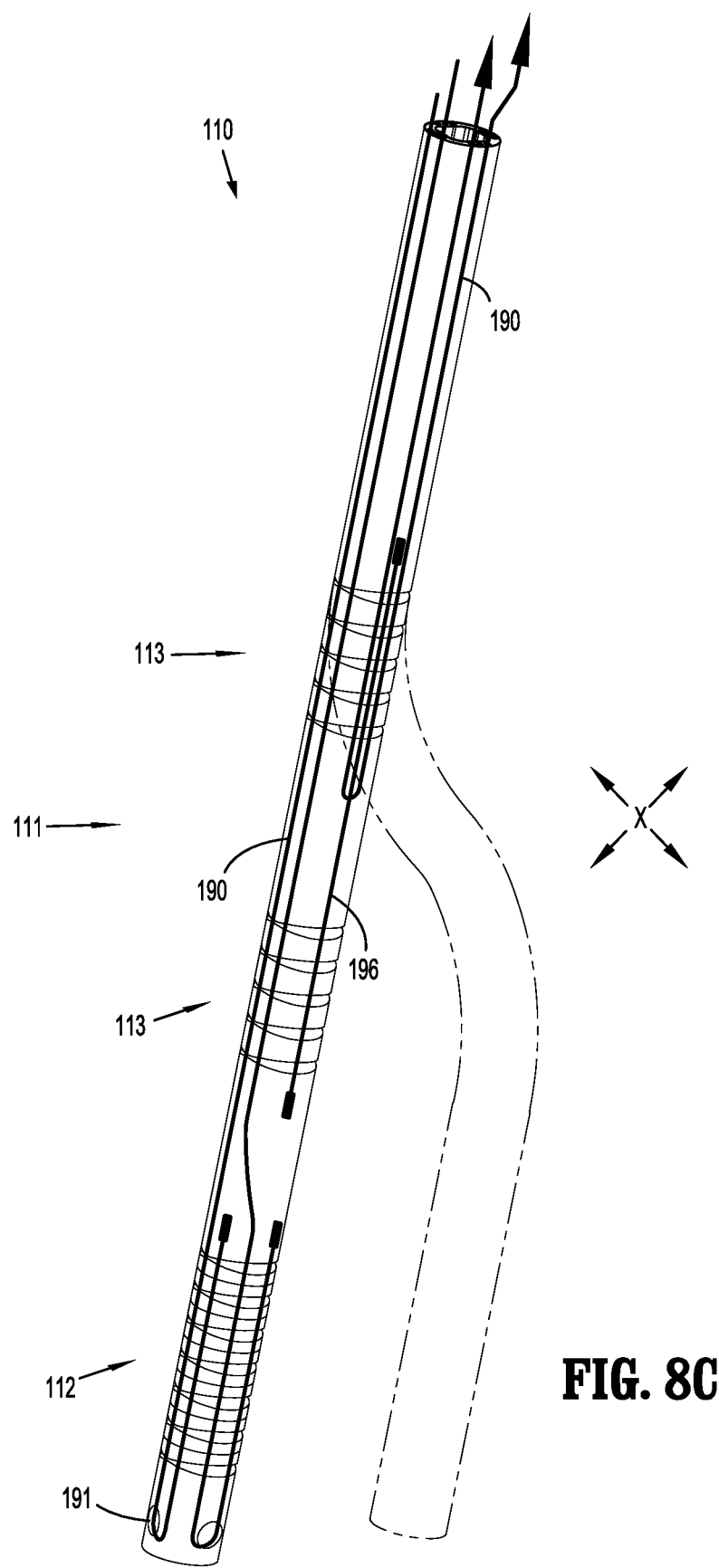
FIG. 8C is a perspective view of the articulable portion of the surgical articulation assembly of FIG. 1, with the first segment articulating in a plane X.

Turning momentarily to FIGS. 8-8C, connecting members 190 are shown diametrically opposed along movable members 114. Connecting members 190 may be arranged such that two diametrically opposed pairs of connecting members 190 terminate in a distal portion of segment 112. As shown, the distal ends 194 of connecting members 190 are secured around diametrically opposed posts 191. The connecting members 190 are looped around posts 191 such that forces exerted through connecting members 190 are transmitted to the second segment 112 through posts 191. A pair of diametrically opposed connecting members 190 may additionally be looped around a portion of first segment 111 between the first and second sets 113 of movable members 114. Additionally, a pair of coupling members 196 are disposed along a central portion of articulable portion 110, such that segments 111 and 112 are coupled. Other arrangements are contemplated for connecting members 190 and coupling members 196. As will be described further in detail below, connecting members 190 cooperate such that opposing forces generated in opposing connecting members 190 will cause articulation of the first and second segments 111, 112 articulable portion 110 through desired planes.

Figure 11:
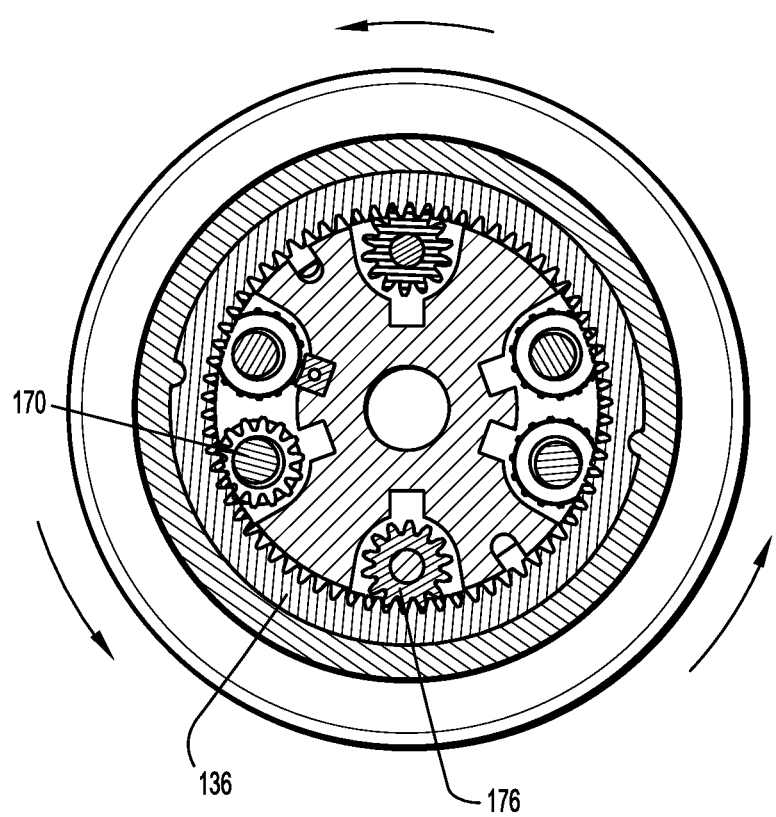
FIG. 11 is a top plan cross-sectional view of the control assembly as shown in FIG. 1.

Referring to FIGS. 2, 8-8C, and 11-12 the operation of surgical articulation assembly 100 is shown. Turning initially to FIG. 2, an operator will insert a surgical object 500 through the passage 102 (FIG. 8). Where the surgical object 500 is an instrument, an end effector 502 will extend through a distal end 103 of the passage 102 and into an internal body cavity (not shown) for use in a minimally invasive procedure. The surgical object 500 will be disposed in the passage 102 such that articulation of the articulable portion 110 will cause the surgical object 500 to move relative to the longitudinal axis A1. Surgical object 500 and surgical articulation assembly 100 may further be inserted through an access member (not shown). As seen in FIG. 11, an operator will rotate a user control 131, 142, 152 (FIG. 3) about the longitudinal axis A1, causing a respective engagement member 136 to engage the rotatable members 176 on a pair of diametrically opposed driving members 170.

Turning to FIG. 12, the motion of the translating members 180 is shown. As the pair of driving members 170 having opposing surface features 179 (right-handed and left-handed threads) are subject to the same rotational force applied by an engagement member 136, the rotation of the diametrically opposed driving members 170 will cause a translating member 180 to translate proximally, and an opposing translating member 180 to translate distally along driving members 170. As the proximal ends 192 of the connecting members 190 are securely disposed in the housing 184 of the translating members 180, connecting members 190 will translate with their respective translating members 180. The attachment of the distal ends 194 of the connecting members to a portion of articulable portion 110 (FIG. 10) effects a tensile or compressive force that results in user controlled articulation.

Referring to FIGS. 8-8C, the articulation of articulable portion 110 will be described. As discussed above, a pair of diametrically opposed connecting members 190 are looped around a portion of the first segment 111 between the first and second sets 113 of movable members 114. The opposed connecting members 190 may be looped around an internal structure such as a hook or tab, or may be partially embedded within a portion of the first segment 111. Upon the exertion of forces through the opposed connecting members 190, the first segment 111 tends to articulate in a plane X as shown. However, the presence of coupling members 196 ensures that the first and second sets 113 of movable members 114 first segment articulates through a limited range of motion defined by the length of the coupling members 196. Additionally, substantially equally numbered sets of movable members 114 on either side of the looped portion of opposed connecting members 190 ensures that the articulation is effected substantially equally on either side of the looped portion of opposed connecting members 190. Accordingly, first segment 111 articulates in such a manner such that proximal set 113 of movable members 114 and the distal set 113 of movable members 114 are disposed substantially parallel and laterally offset from each other by virtue of the coupling members 196. In this way, an operator may effect articulation of first segment 111 such that the second segment 112 is offset but substantially parallel to the longitudinal axis A1. Thus, an operator may engage first user control 131 to dispose the portions of the first and second segments 111, 112 along axes laterally spaced from the longitudinal axis A1. It should be noted that while first user control 131 is discussed here as effecting articulation of the first segment 111 in plane X, first control assembly 130 may be configured to effect articulation of first segment 111 through any desired plane.

When second user control 142 (FIG. 3) is rotated about the longitudinal axis A1, the engagement member 136, rotatable member 176, opposing driving members 170, and translating members 180 cause a pair of diametrically opposed connecting members 190 attached to a portion of the second segment 112 to exert a force that effects articulation in plane X as shown. The diametrically opposed connecting members 190 allow for bi-directional movement within plane X upon rotating the user control 131 in a clockwise or counter-clockwise direction by exerting axially opposing forces on opposing sides of the first segment 111. Rotation of user control 152 (FIG. 3) causes a pair of diametrically opposed connecting members 190 terminating in the second segment 112 to articulate second segment 112 in a plane Y that is substantially transverse to plane X, as shown. As plane X and plane Y are substantially transverse, the pair of connecting members 190 effecting articulation in plane X and the pair of connecting members 190 effecting articulation in plane Y are radially spaced in second segment 112. Thus, the coordination of second and third user controls 142, 152 allows an operator to articulate second segment 112 bi-directionally in each of plane X and transverse plane Y. It should be noted that planes X and Y may represent any spatial planes that are substantially transverse.

Accordingly, an operator may manipulate first, second, and third user controls 131, 142, 152 in a manner such that the articulable portion 110 is used to reach off axis points in a minimally invasive surgical site. It should be noted that the first, second, and third user controls 131, 142, 152 may be associated with any arrangement of the sets of connecting members 190.

It will be understood that various modifications may be made to the embodiments disclosed herein. Therefore, the above description should not be construed as limiting, but merely as exemplifications of embodiments. Those skilled in the art will envision other modifications within the scope and spirit of the present disclosure.

What is claimed is:

1. A surgical articulation assembly comprising:
   a first articulation assembly including:
      a first engaging member rotatable about a longitudinal axis; and
      a first actuation assembly operably coupled to the first engaging member and to a first segment of an elongate member such that rotation of the first engaging member causes displacement of the first segment;
   a second articulation assembly including:
      a second engaging member rotatable about the longitudinal axis; and
      a second actuation assembly operably coupled to the second engaging member and to a second segment of the elongate member such that rotation of the second engaging member causes displacement of the second segment in a first plane; and
   a third articulation assembly including:
      a third engaging member rotatable about the longitudinal axis; and
      a third actuation assembly operably coupled to the third engaging member and to the second segment of the elongate member such that rotation of the third engaging member causes displacement of the second segment in a second plane.

2. The surgical articulation assembly of claim 1, wherein at least one of the first, second, or third actuation assemblies includes at least one rotatable member operably coupled to a corresponding first, second, or third engaging member such that rotation of the corresponding first, second, or third engaging member causes rotation of the at least one rotatable member.

3. The surgical articulation assembly of claim 2, wherein the at least one rotatable member is an elongate member having threads.

4. The surgical articulation assembly of claim 2, wherein the at least one rotatable member is configured to rotate about an axis laterally spaced from the longitudinal axis.

5. The surgical articulation assembly of claim 4, wherein the first actuation assembly includes a first connecting member configured to connect the first actuation assembly to the first segment of the elongate member, the at least one translatable member being attached to a portion of the first connecting member.

6. The surgical articulation assembly of claim 2, wherein at least one of the first, second, or third actuation assemblies includes at least one translatable member in mechanical cooperation with the at least one rotatable member.

7. The surgical articulation assembly of claim 6, wherein the at least one translatable member translates along a portion of the at least one rotatable member.

8. The surgical articulation assembly of claim 1, wherein at least one of the first, second, or third actuation assemblies includes diametrically opposing rotatable members.

9. The surgical articulation assembly of claim 8, wherein the diametrically opposing rotatable members have threads in opposite directions.

10. The surgical articulation assembly of claim 1, wherein the first articulation assembly includes a first user control structure defining a throughhole dimensioned to receive the first engaging member therein.

11. The surgical articulation assembly of claim 1, wherein the second and third articulation assemblies further include respective second and third user control structures mechanically engaged with the respective second and third engaging members, the second and third user control structures being rotatable and coaxially disposed about the longitudinal axis.

12. The surgical articulation assembly of claim 10, wherein the first user control structure further includes at least one protrusion disposed on an inner facing surface thereof, and the first engaging member defining at least one recess on an outer surface thereof, the at least one protrusion engageable with the at least one recess.

13. The surgical articulation assembly of claim 1, wherein the first plane is transverse to the second plane.

14. A surgical articulation assembly comprising:
 a first articulation assembly including:
  a first engaging member; and
  a first actuation assembly operably coupled to the first engaging member and to a first segment of an elongate member;
 a second articulation assembly including:
  a second engaging member; and
  a second actuation assembly operably coupled to the second engaging member and to a second segment of the elongate member such that rotation of the second engaging member causes displacement of the second segment in a first plane; and
 a third articulation assembly including:
  a third engaging member; and
  a third actuation assembly operably coupled to the third engaging member and to the second segment of the elongate member such that rotation of the third engaging member causes displacement of the second segment in a second plane.

15. The surgical articulation assembly of claim 14, wherein at least one of the first, second, or third actuation assemblies includes at least one rotatable member operably coupled to a corresponding first, second, or third engaging member such that rotation of the corresponding first, second, or third engaging member causes rotation of the at least one rotatable member.

16. The surgical articulation assembly of claim 15, wherein the at least one rotatable member is configured to rotate about an axis laterally spaced from a longitudinal axis defined by the first engaging member.

17. The surgical articulation assembly of claim 15, wherein at least one of the first, second, or third actuation assemblies includes at least one translatable member in mechanical cooperation with the at least one rotatable member.

18. The surgical articulation assembly of claim 14, wherein at least one of the first, second, or third actuation assemblies includes diametrically opposing rotatable members.

19. A surgical articulation assembly comprising:
 a first actuation assembly including a first connecting member configured to couple the first actuation assembly to a first segment of an elongate member such that actuation of the first actuation assembly causes displacement of the first segment;
 a second actuation assembly including a second connecting member configured to couple the second actuation assembly to a second segment of the elongate member such that actuation of the second actuation assembly causes displacement of the second segment in a first plane; and
 a third actuation assembly including a third connecting member configured to couple the third actuation assembly to the second segment such that actuation of the third actuation assembly causes displacement of the second segment in a second plane.

* * * * *